US009441037B2

(12) United States Patent
Ward et al.

(10) Patent No.: US 9,441,037 B2
(45) Date of Patent: *Sep. 13, 2016

(54) METHODS FOR REDUCING EXACERBATION RATES OF ASTHMA USING BENRALIZUMAB

(71) Applicant: MedImmune, LLC, Gaithersburg, MD (US)

(72) Inventors: Christine Ward, Gaithersburg, MD (US); Lorin Roskos, Gaithersburg, MD (US); Bing Wang, Gaithersburg, MD (US); Donald Raible, Berwyn, PA (US)

(73) Assignee: ASTRAZENECA AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/453,942

(22) Filed: Aug. 7, 2014

(65) Prior Publication Data

US 2015/0044202 A1    Feb. 12, 2015

Related U.S. Application Data

(60) Provisional application No. 61/864,944, filed on Aug. 12, 2013.

(51) Int. Cl.
| C07K 16/28 | (2006.01) |
| A61K 45/06 | (2006.01) |
| A61K 39/395 | (2006.01) |
| C07K 16/24 | (2006.01) |
| A61K 39/00 | (2006.01) |

(52) U.S. Cl.
CPC ....... *C07K 16/244* (2013.01); *A61K 2039/505* (2013.01); *A61K 2039/545* (2013.01); *C07K 2317/24* (2013.01)

(58) Field of Classification Search
None
See application file for complete search history.

(56) References Cited

U.S. PATENT DOCUMENTS

| 6,018,032 | A | 1/2000 | Koike et al. |
| 6,538,111 | B1 | 3/2003 | Koike et al. |
| 6,746,839 | B1 * | 6/2004 | Duff et al. ................ 435/6.14 |
| 6,946,292 | B2 | 9/2005 | Kanda et al. |
| 7,179,464 | B2 | 2/2007 | Koike et al. |
| 7,214,775 | B2 | 5/2007 | Hanai et al. |
| 7,238,354 | B2 | 7/2007 | Koike et al. |
| 7,393,683 | B2 | 7/2008 | Kanda et al. |
| 7,404,953 | B2 | 7/2008 | Hosaka et al. |
| 7,425,446 | B2 | 9/2008 | Kanda et al. |
| 7,662,925 | B2 | 2/2010 | Lazar et al. |
| 7,708,992 | B2 | 5/2010 | Hanai et al. |
| 7,718,175 | B2 | 5/2010 | Hanai et al. |
| 7,737,325 | B2 | 6/2010 | Kanda et al. |
| 7,741,442 | B2 | 6/2010 | Kanda et al. |
| 7,846,725 | B2 | 12/2010 | Kanda et al. |
| 8,501,176 | B2 * | 8/2013 | Koike et al. ............ 424/133.1 |
| 2006/0014680 | A1 | 1/2006 | Xu et al. |
| 2006/0063254 | A1 | 3/2006 | Kanda et al. |
| 2007/0003546 | A1 | 1/2007 | Lazar et al. |
| 2010/0291073 | A1 * | 11/2010 | Koike et al. ............ 424/133.1 |
| 2012/0156194 | A1 | 6/2012 | Arron et al. |
| 2012/0328606 | A1 | 12/2012 | Gossage et al. |
| 2014/0004109 | A1 | 1/2014 | Koike et al. |
| 2014/0328839 | A1 | 11/2014 | Molfino et al. |
| 2015/0044203 | A1 | 2/2015 | Ward et al. |
| 2015/0044204 | A1 | 2/2015 | Ward et al. |

FOREIGN PATENT DOCUMENTS

| EP | 1266663 A1 | 12/2002 |
| EP | 1688437 A1 | 9/2006 |
| WO | WO97/10354 | 3/1997 |
| WO | WO00/61739 | 10/2000 |
| WO | WO 01/60405 A1 | 8/2001 |
| WO | WO2007/041635 A2 | 12/2007 |
| WO | WO2013/066780 A2 | 10/2013 |

OTHER PUBLICATIONS

Kolbeck et al. (2010), J. Allergy Clin Immunol., vol. 125, pp. 1344-1353.*
Busse et al. (2010), J. Allergy Clin Immunol., vol. 125, pp. 1237-1244.*
NCT00768079 (2008), p. 1-4.*
Busse, William W. et al., 2010, "Safety profile, pharmacokinetics, and biologic activity of MEDI-563, an anti-IL-5 receptor α antibody, in a phase I study of subjects with mild asthma", J. Allergy Clin. Immunol. 125:1237-1244.
Chihara. Junichi et al., 1990, "Characterization of a Receptor for Interleukin 5 on Human Eosinophils: Variable Expression and Induction by Granulocyte/Macrophage Colony-stimulating Factor", J. Exp. Med., 172: 1347-1351.
Corrigan, C.J. et al., 1992, "T cells and eosinophils in the pathogensis of asthma", Immunology Today, 13(12): 501-506.
Ema, Hideo et al., 1990, "Target Cells for Granulocyte Colony-Stimulating Factor, Interleukin-3, and Interleukin-5 In Differentation Pathways of Neutrophils and Eosinophils", 76(10): 1956-1961.
Farinacci, Charles J. et al., 1951, "Eosinophilic Granuloma of the Lung", United States Armed Forces Medical Journal, vol. 11(7):1085-1093.
Fauci, Anthony S. et al., 1982, "The Idiopathic Hypereosinophilic Syndrome", Annals of Internal Medicine, 97:78-92.
Fukuda, Takeshi et al., 1985, "Increased Numbers of Hypodense Eosinophils in the Blood of Patients with Bronchial Asthma", Am. Rev. Respir. Dis. 132:981-985.
Garrett, Jennifer K. Et al., 2004, "Anti-interleukin-5 (mepolizumab) therapy for hypereosinophilic syndromes", J. Allergy Clin. Immumol. 113:115-119.
Gleich, Gerald J. et al., 1986, "The Eosinophilic Leukocyte: Structure and Function", Advances in Immunology, 39:177-253.
Green, Ruth H. et al., 2002, "Asthma exacerbations and spurum eosinophil counts: a randomised controlled trial", Lancet, 360:1715-1721.
Gruart, Valerie et al., 1989, "Variations In Protein Expression Related to Human Eosinophil Heterogeneity", The Journal of Immunology, 142:4416-4421.

(Continued)

*Primary Examiner* — Christine J Saoud
*Assistant Examiner* — Jegatheesan Seharaseyon

(57) ABSTRACT

Provided herein is are methods of reducing exacerbations of asthma in an asthma patient, comprising administering to the patient an effective amount of the anti-interleukin-5 receptor (IL-5R) antibody benralizumab or an antigen-binding fragment thereof.

9 Claims, 9 Drawing Sheets

(56) References Cited

OTHER PUBLICATIONS

Haldar, Pranabashis et al., 2009, "Mepolizumab and Exacerbations of Refractory Eosinophilic Asthma", The New England Journal of Medicine, 360:973-984.

Harley, John B. et al., 1983, "Noncardiovascular Findings Associated with Heart Disease in the Idiopathic Hypercosinophilic Syndrome", Am. J. Cardiol., 52:321-324.

Ishino, Tetsuya et al., 2004, "Kinetic Interaction Analysis of Human Interleukin 5 Receptor α Mutants Reveals a Unique Binding Topology and Charge Distribution for Cytokine Recognition", J. Biol. Chem., 279(10):9547-9556.

International Search Report corresponding to PCT/US2008/06156 mailed Sep. 25, 2008.

International Search Report corresponding PCT/US2014/050080 mailed Dec. 5, 2014.

Kolbeck, Roland, 2010, "MEDI-563, a humanized anti-IL-5 receptor α mAb with enhanced antibody-dependent cell-mediated cytotoxicity function", J. Allergy Clin. Immunol. 125:1344-1353.

Owen, William F. et al., 1989, "Interleukin 5 and Phenotypically Altered Eosinophils in the Blood of Patients with the Idiopathicf Hypereosinophilic Syndrome", J. Exp. Med., 170:343-348.

Rothenberg, Marc. E. et al., 1988, "Human Eosinophils Have Prolonged Survival, Enhanced Functional Properties, and Become Hypodense When Exposed to Human Interleukin 3", J. Clin. Invest., 81:1986-1992.

Saito, Hirohisa et al., 1988, "Selective differentiation and proliferation of hematopoietic cells induced by recombinant human interleukins", Proc. Natl. Acad. Sci. USA, 85:2288-2292.

Saita, Naoki et al., 1999, "Difference in Apoptotic Function between Eosinophils from Peripheral Blood and Bronchoalveolar Lavage in Chronic Eosinophilic Pneumonia", Int. Arch. Allergy Immunol., 120:91-94.

Spry, C.J.F. et al., 1976, "Studies on blood cosinophils", Clin. Exp. Immunol. 24:423-434.

Tai, P.C., et al., 1991, "Effects of IL-5, granulocyte/macrophage colony-stimulating factor (GM-CSF) and IL-3 on the survival of human blood eosinophils in vitro", Clin. Exp. Immunol., 85:312-316.

Teran, L. M. et al., 1996, "The chemokines: their potential role in allergic inflammation", Clinical and Experimental Allergy, 26:1005-1019.

Winqvist, I. et al., 1982, "Altered density, metabolism and surface receptors of eosinophils in eosinophilia", Immunology, 47:531-539.

Lazar, GA et al., 2006 "Engineered antibody Fc variants with enhanced effector function", Proceedings of the National Academy of Sciences, vol. 103, No. 11, pp. 4005-4010.

Siberil, Sophie et al., 2007, "FegammaR: The Key to Optimize Therapeutic Antibodies?", Critical Reviews in Oncology/Hematology, Elsevier Science Ireland Ltd., Limerick, IE., vol. 62, No. 1, pp. 26-33.

Supplementary European Search Report for EP 08779619 dated May 12, 2012.

English Translation of Kyowa Hakko, Clinical study on an antibody medicinal product for treating asthma, over 6 years by the US subsidiary, Chemical Daily, Nov. 2, 2005, Chemical Daily p. 6, (No. 378).

English Translation of Official Action dated Apr. 2, 2013 for corresponding Japanese Application No. 2010-508412.

\* cited by examiner

Exacerbation Rate by Blood Eosinophil Count

| EOS | | | Interim Analysis | | | | Stage I Analysis | | |
|---|---|---|---|---|---|---|---|---|---|
| | Treatment Group | N | Rate | Reduction | p-value | N | Rate | Reduction | p-value |
| <300 | Placebo | 139 | 0.48 | | | 139 | 0.49 | | |
| | 2mg | 16 | 0.25 | 47% | --- | 16 | 0.21 | 57% | --- |
| | 20mg | 11 | 0.75 | --- | --- | 11 | 0.82 | --- | --- |
| | 100mg | 124 | 0.40 | 18% | 0.481 | 124 | 0.42 | 16% | 0.479 |
| ≥ 300 | Placebo | 83 | 0.65 | | | 83 | 0.68 | | |
| | 2mg | 65 | 0.66 | 1% | 0.987 | 65 | 0.75 | --- | 0.822 |
| | 20mg | 70 | 0.24 | 63% | 0.011 | 70 | 0.30 | 57% | 0.014 |
| | 100mg | 97 | 0.38 | 41% | 0.073 | 97 | 0.38 | 43% | 0.049 |

Figure 2

Exacerbation Rate by Baseline ICS Status

| ICS | Treatment Group | Interim Analysis | | | | Stage I Analysis | | | |
|---|---|---|---|---|---|---|---|---|---|
| | | N | Rate | Reduction | p-value | N | Rate | Reduction | p-value |
| Medium | Placebo | 122 | 0.52 | | | 122 | 0.52 | | |
| | 2mg | 41 | 0.39 | 25% | 0.473 | 39* | 0.42 | 19% | 0.578 |
| | 20mg | 39 | 0.24 | 53% | 0.125 | 39 | 0.28 | 46% | 0.169 |
| | 100mg | 117 | 0.30 | 42% | 0.064 | 117 | 0.33 | 37% | 0.100 |
| High | Placebo | 100 | 0.57 | | | 100 | 0.62 | | |
| | 2mg | 40 | 0.80 | --- | 0.378 | 42* | 0.85 | --- | 0.326 |
| | 20mg | 42 | 0.39 | 33% | 0.370 | 42 | 0.46 | 25% | 0.436 |
| | 100mg | 105 | 0.49 | 14% | 0.598 | 105 | 0.48 | 22% | 0.331 |

*: Additional baseline ICS information was added after interim for two subjects.

Figure 3

Exacerbation Rate by Blood Eosinophil Count and Baseline ICS Status

| ICS | | Interim Analysis | | | | Stage I Analysis | | | |
|---|---|---|---|---|---|---|---|---|---|
| | Treatment Group | N | Rate | Reduction | p-value | N | Rate | Reduction | p-value |
| ICS=Medium EOS<300 | Placebo | 79 | 0.51 | | | 79 | 0.51 | | |
| | 2mg | 9 | 0.47 | 9% | -- | 7 | 0.49 | 4% | -- |
| | 20mg | 4 | 0.85 | -- | -- | 4 | 1.00 | -- | -- |
| | 100mg | 63 | 0.29 | 44% | 0.167 | 63 | 0.33 | 37% | 0.233 |
| ICS=High EOS<300 | Placebo | 60 | 0.43 | | | 60 | 0.47 | | |
| | 2mg | 7 | 0.00 | 100% | -- | 9 | 0.00 | 100% | -- |
| | 20mg | 7 | 0.68 | -- | -- | 7 | 0.71 | -- | -- |
| | 100mg | 61 | 0.51 | | 0.682 | 61 | 0.51 | -- | 0.795 |

Figure 4

Exacerbation Rate by Blood Eosinophil Count and Baseline ICS Status

| ICS | Treatment Group | Interim Analysis | | | Stage I Analysis | | |
|---|---|---|---|---|---|---|---|
| | | N | Rate | Reduction | p-value | N | Rate | Reduction | p-value |

| ICS | Treatment Group | N | Rate | Reduction | p-value | N | Rate | Reduction | p-value |
|---|---|---|---|---|---|---|---|---|---|
| ICS=Medium EOS ≥ 300 | Placebo | 43 | 0.53 | | | 43 | 0.52 | | |
| | 2mg | 32 | 0.37 | 29% | 0.475 | 32 | 0.41 | 22% | 0.583 |
| | 20mg | 35 | 0.17 | 67% | 0.039 | 35 | 0.19 | 64% | 0.044 |
| | 100mg | 54 | 0.31 | 41% | 0.216 | 54 | 0.32 | 38% | 0.264 |
| ICS=High EOS ≥ 300 | Placebo | 40 | 0.80 | | | 40 | 0.86 | | |
| | 2mg | 33 | 0.97 | --- | 0.668 | 33 | 1.07 | --- | 0.566 |
| | 20mg | 35 | 0.32 | 60% | 0.102 | 35 | 0.41 | 52% | 0.118 |
| | 100mg | 43 | 0.47 | 42% | 0.201 | 43 | 0.46 | 46% | 0.102 |

Figure 5

Exacerbations by Baseline EOS Count

| EOS Counts Cut-off | Treatment Group | N | Exacerbation Rate Ratio (90% CI) | Rate Reduction (%) | p-value |
|---|---|---|---|---|---|
| ≥150 | Placebo** | 158 | | | |
| | 2 mg | 76 | 1.23 (0.77, 1.97) | | 0.475 |
| | 20mg | 78 | 0.65 (0.38, 1.14) | 35 | 0.206 |
| | 100mg** | 171 | 0.63 (0.42, 0.94) | 37 | 0.056 |
| <150 | Placebo | 64 | | | |
| | 2 mg | 5 | | | |
| | 20mg | 3 | | | |
| | 100mg | 50 | 0.97 (0.53, 1.80) | 3 | 0.941 |
| ≥200 | Placebo | 139 | | | |
| | 2 mg | 75 | 1.24 (0.77, 2.01) | | 0.457 |
| | 20mg | 78 | 0.67 (0.39, 1.15) | 33 | 0.224 |
| | 100mg | 151 | 0.67 (0.44, 1.01) | 33 | 0.110 |
| <200 | Placebo | 83 | | | |
| | 2 mg | 6 | | | |
| | 20mg | 3 | | | |
| | 100mg | 70 | 0.82 (0.46, 1.45) | 18 | 0.565 |

Figure 7A

Exacerbations by Baseline EOS Count

| EOS Counts Cut-off | Treatment Group | N | Exacerbation Rate Ratio (90% CI) | Rate Reduction (%) | p-value |
|---|---|---|---|---|---|
| ≥300 | Placebo** | 83 | | | |
| | 2 mg | 65 | 0.99 (0.59, 1.68) | 1 | 0.987 |
| | 20mg | 70 | 0.37 (0.19, 0.70) | 63 | 0.011 |
| | 100mg** | 97 | 0.59 (0.36, 0.96) | 41 | 0.073 |
| <300 | Placebo | 139 | | | |
| | 2 mg | 16 | 0.53 (0.14, 1.95) | | 0.423 |
| | 20mg | 11 | 1.62 (0.65, 4.00) | | 0.385 |
| | 100mg | 124 | 0.82 (0.54, 4.31) | 18 | 0.481 |
| ≥400 | Placebo | 52 | | | |
| | 2 mg | 50 | 0.90 (0.51, 1.60) | 10 | 0.765 |
| | 20mg | 53 | 0.36 (0.17, 0.78) | 64 | 0.028 |
| | 100mg | 58 | 0.36 (0.18, 0.72) | 64 | 0.015 |
| <400 | Placebo | 170 | | | |
| | 2 mg | 31 | 1.17 (0.57, 2.39) | | 0.721 |
| | 20mg | 28 | 0.92 (0.44, 1.93) | 8 | 0.852 |
| | 100mg | 163 | 0.87 (0.59, 1.29) | 13 | 0.566 |

Figure 7B

SEQUENCE LISTING

<160> NUMBER OF SEQ ID NOS: 12

<210> SEQ ID NO 1
<211> LENGTH: 107
<212> TYPE: PRT
<213> ORGANISM: Homo sapiens

<400> SEQUENCE: 1

```
Asp Ile Gln Met Thr Gln Ser Pro Ser Ser Leu Ser Ala Ser Val Gly
1               5                   10                  15
Asp Arg Val Thr Ile Thr Cys Gly Thr Ser Glu Asp Ile Ile Asn Tyr
            20                  25                  30
Leu Asn Trp Tyr Gln Gln Lys Pro Gly Lys Ala Pro Lys Leu Leu Ile
        35                  40                  45
Tyr His Thr Ser Arg Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Tyr Thr Leu Pro Tyr
                85                  90                  95
Thr Phe Gly Gln Gly Thr Lys Val Glu Ile Lys
            100                 105
```

<210> SEQ ID NO 2
<211> LENGTH: 214
<212> TYPE: PRT
<213> ORGANISM: Homo sapiens

<400> SEQUENCE: 2

```
Asp Ile Gln Met Thr Gln Ser Pro Ser Ser Leu Ser Ala Ser Val Gly
1               5                   10                  15
Asp Arg Val Thr Ile Thr Cys Gly Thr Ser Glu Asp Ile Ile Asn Tyr
            20                  25                  30
Leu Asn Trp Tyr Gln Gln Lys Pro Gly Lys Ala Pro Lys Leu Leu Ile
        35                  40                  45
Tyr His Thr Ser Arg Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Tyr Thr Leu Pro Tyr
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

```
<210> SEQ ID NO 3
<211> LENGTH: 121
<212> TYPE: PRT
<213> ORGANISM: Homo sapiens

<400> SEQUENCE: 3
```

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Val Ile His Trp Val Arg Gln Arg Pro Gly Gln Gly Leu Ala Trp Met
            35                  40                  45
Gly Tyr Ile Asn Pro Tyr Asn Asp Gly Thr Lys Tyr Asn Glu Arg Phe
        50                  55                  60
Lys Gly Lys Val Thr Ile Thr Ser Asp Arg Ser Thr Ser Thr Val Tyr
65                  70                  75                  80
Met Glu Leu Ser Ser Leu Arg Ser Glu Asp Thr Ala Val Tyr Leu Cys
                85                  90                  95
Gly Arg Glu Gly Ile Arg Tyr Tyr Gly Leu Leu Gly Asp Tyr Trp Gly
            100                 105                 110
Gln Gly Thr Leu Val Thr Val Ser Ser
        115                 120
```

```
<210> SEQ ID NO 4
<211> LENGTH: 451
<212> TYPE: PRT
<213> ORGANISM: Homo sapiens

<400> SEQUENCE: 4
```

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Val Ile His Trp Val Arg Gln Arg Pro Gly Gln Gly Leu Ala Trp Met
            35                  40                  45
Gly Tyr Ile Asn Pro Tyr Asn Asp Gly Thr Lys Tyr Asn Glu Arg Phe
        50                  55                  60
Lys Gly Lys Val Thr Ile Thr Ser Asp Arg Ser Thr Ser Thr Val Tyr
65                  70                  75                  80
Met Glu Leu Ser Ser Leu Arg Ser Glu Asp Thr Ala Val Tyr Leu Cys
                85                  90                  95
Gly Arg Glu Gly Ile Arg Tyr Tyr Gly Leu Leu Gly Asp Tyr Trp Gly
            100                 105                 110
```

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 5
<211> LENGTH: 400
<212> TYPE: PRT
<213> ORGANISM: Homo sapiens

<400> SEQUENCE: 5

Asp Leu Leu Pro Asp Glu Lys Ile Ser Leu Leu Pro Pro Val Asn Phe
1               5                   10                  15

Thr Ile Lys Val Thr Gly Leu Ala Gln Val Leu Leu Gln Trp Lys Pro
            20                  25                  30

Asn Pro Asp Gln Glu Gln Arg Asn Val Asn Leu Glu Tyr Gln Val Lys
            35                  40                  45

Ile Asn Ala Pro Lys Glu Asp Tyr Glu Thr Arg Ile Thr Glu Ser
 50                  55                  60

Lys Cys Val Thr Ile Leu His Lys Gly Phe Ser Ala Ser Val Arg Thr
 65                  70                  75                  80

Ile Leu Gln Asn Asp His Ser Leu Leu Ala Ser Ser Trp Ala Ser Ala
                85                  90                  95

Glu Leu His Ala Pro Pro Gly Ser Pro Gly Thr Ser Ile Val Asn Leu
            100                 105                 110

Thr Cys Thr Thr Asn Thr Thr Glu Asp Asn Tyr Ser Arg Leu Arg Ser
            115                 120                 125

Tyr Gln Val Ser Leu His Cys Thr Trp Leu Val Gly Thr Asp Ala Pro
            130                 135                 140

Glu Asp Thr Gln Tyr Phe Leu Tyr Tyr Arg Tyr Gly Ser Trp Thr Glu
145                 150                 155                 160

Glu Cys Gln Glu Tyr Ser Lys Asp Thr Leu Gly Arg Asn Ile Ala Cys
                165                 170                 175

Trp Phe Pro Arg Thr Phe Ile Leu Ser Lys Gly Arg Asp Trp Leu Ala
            180                 185                 190

Val Leu Val Asn Gly Ser Ser Lys His Ser Ala Ile Arg Pro Phe Asp
            195                 200                 205

Gln Leu Phe Ala Leu His Ala Ile Asp Gln Ile Asn Pro Pro Leu Asn
            210                 215                 220

Val Thr Ala Glu Ile Glu Gly Thr Arg Leu Ser Ile Gln Trp Glu Lys
225                 230                 235                 240

Pro Val Ser Ala Phe Pro Ile His Cys Phe Asp Tyr Glu Val Lys Ile
                245                 250                 255

His Asn Thr Arg Asn Gly Tyr Leu Gln Ile Glu Lys Leu Met Thr Asn
            260                 265                 270

Ala Phe Ile Ser Ile Ile Asp Asp Leu Ser Lys Tyr Asp Val Gln Val
            275                 280                 285

Arg Ala Ala Val Ser Ser Met Cys Arg Glu Ala Gly Leu Trp Ser Glu
            290                 295                 300

Trp Ser Gln Pro Ile Tyr Val Gly Asn Asp Glu His Lys Pro Leu Arg
305                 310                 315                 320

Glu Trp Phe Val Ile Val Ile Met Ala Thr Ile Cys Phe Ile Leu Leu
                325                 330                 335

Ile Leu Ser Leu Ile Cys Lys Ile Cys His Leu Trp Ile Lys Leu Phe
            340                 345                 350

Pro Pro Ile Pro Ala Pro Lys Ser Asn Ile Lys Asp Leu Phe Val Thr
            355                 360                 365

Thr Asn Tyr Glu Lys Ala Gly Ser Ser Glu Thr Glu Ile Glu Val Ile
            370                 375                 380

Cys Tyr Ile Glu Lys Pro Gly Val Glu Thr Leu Glu Asp Ser Val Phe
385                 390                 395                 400

<210> SEQ ID NO 6
<211> LENGTH: 398
<212> TYPE: PRT
<213> ORGANISM: Mus musculus

<400> SEQUENCE: 6

Asp Leu Leu Asn His Lys Lys Phe Leu Leu Leu Pro Pro Val Asn Phe

```
              1               5                    10                   15
            Thr Ile Lys Ala Thr Gly Leu Ala Gln Val Leu Leu His Trp Asp Pro
                            20                  25                  30

Asn Pro Asp Gln Glu Gln Arg His Val Asp Leu Glu Tyr His Val Lys
                            35                  40                  45

Ile Asn Ala Pro Gln Glu Asp Glu Tyr Asp Thr Arg Lys Thr Glu Ser
                            50                  55                  60

Lys Cys Val Thr Pro Leu His Glu Gly Phe Ala Ala Ser Val Arg Thr
             65                  70                  75                  80

Ile Leu Lys Ser Ser His Thr Thr Leu Ala Ser Ser Trp Val Ser Ala
                            85                  90                  95

Glu Leu Lys Ala Pro Pro Gly Ser Pro Gly Thr Ser Val Thr Asn Leu
                            100                 105                 110

Thr Cys Thr Thr His Thr Val Val Ser Ser His Thr His Leu Arg Pro
                            115                 120                 125

Tyr Gln Val Ser Leu Arg Cys Thr Trp Leu Val Gly Lys Asp Ala Pro
                            130                 135                 140

Glu Asp Thr Gln Tyr Phe Leu Tyr Tyr Arg Phe Gly Val Leu Thr Glu
            145                 150                 155                 160

Lys Cys Gln Glu Tyr Ser Arg Asp Ala Leu Asn Arg Asn Thr Ala Cys
                            165                 170                 175

Trp Phe Pro Arg Thr Phe Ile Asn Ser Lys Gly Phe Glu Gln Leu Ala
                            180                 185                 190

Val His Ile Asn Gly Ser Ser Lys Arg Ala Ala Ile Lys Pro Phe Asp
                            195                 200                 205

Gln Leu Phe Ser Pro Leu Ala Ile Asp Gln Val Asn Pro Pro Arg Asn
                            210                 215                 220

Val Thr Val Glu Ile Glu Ser Asn Ser Leu Tyr Ile Gln Trp Glu Lys
            225                 230                 235                 240

Pro Leu Ser Ala Phe Pro Asp His Cys Phe Asn Tyr Glu Leu Lys Ile
                            245                 250                 255

Tyr Asn Thr Lys Asn Gly His Ile Gln Lys Glu Lys Leu Ile Ala Asn
                            260                 265                 270

Lys Phe Ile Ser Lys Ile Asp Asp Val Ser Thr Tyr Ser Ile Gln Val
                            275                 280                 285

Arg Ala Ala Val Ser Ser Pro Cys Arg Met Pro Gly Arg Trp Gly Glu
                            290                 295                 300

Trp Ser Gln Pro Ile Tyr Val Gly Lys Glu Arg Lys Ser Leu Val Glu
            305                 310                 315                 320

Trp His Leu Ile Val Leu Pro Thr Ala Ala Cys Phe Val Leu Leu Ile
                            325                 330                 335

Phe Ser Leu Ile Cys Arg Val Cys His Leu Trp Thr Arg Leu Phe Pro
                            340                 345                 350

Pro Val Pro Ala Pro Lys Ser Asn Ile Lys Asp Leu Pro Val Val Thr
                            355                 360                 365

Glu Tyr Glu Lys Pro Ser Asn Glu Thr Lys Ile Glu Val Val His Cys
                            370                 375                 380

Val Glu Glu Val Gly Phe Glu Val Met Gly Asn Ser Thr Phe
            385                 390                 395

<210> SEQ ID NO 7
<211> LENGTH: 5
<212> TYPE: PRT
<213> ORGANISM: Homo sapiens
```

```
<400> SEQUENCE: 7

Ser Tyr Val Ile His
1               5

<210> SEQ ID NO 8
<211> LENGTH: 17
<212> TYPE: PRT
<213> ORGANISM: Homo sapiens

<400> SEQUENCE: 8

Tyr Ile Asn Pro Tyr Asn Asp Gly Thr Lys Tyr Asn Glu Arg Phe Lys
1               5                   10                  15

Gly

<210> SEQ ID NO 9
<211> LENGTH: 12
<212> TYPE: PRT
<213> ORGANISM: Homo sapiens

<400> SEQUENCE: 9

Glu Gly Ile Arg Tyr Tyr Gly Leu Leu Gly Asp Tyr
1               5                   10

<210> SEQ ID NO 10
<211> LENGTH: 11
<212> TYPE: PRT
<213> ORGANISM: Homo sapiens

<400> SEQUENCE: 10

Gly Thr Ser Glu Asp Ile Ile Asn Tyr Leu Asn
1               5                   10

<210> SEQ ID NO 11
<211> LENGTH: 7
<212> TYPE: PRT
<213> ORGANISM: Homo sapiens

<400> SEQUENCE: 11

His Thr Ser Arg Leu Gln Ser
1               5

<210> SEQ ID NO 12
<211> LENGTH: 9
<212> TYPE: PRT
<213> ORGANISM: Homo sapiens

<400> SEQUENCE: 12

Gln Gln Gly Tyr Thr Leu Pro Tyr Thr
1               5
```

METHODS FOR REDUCING EXACERBATION RATES OF ASTHMA USING BENRALIZUMAB

CROSS REFERENCE TO RELATED APPLICATIONS

This application claims benefit under 35 U.S.C. §119(e) of U.S. Provisional Application No. 61/864,944 filed Aug. 12, 2013. The above listed application is incorporated by reference herein in its entirety for all purposes.

REFERENCE TO THE SEQUENCE LISTING

This application incorporates by reference a Sequence Listing submitted with this application as text file entitled IL5R-603US1_SL.txt created on Jul. 16, 2014 and having a size of 16,022 bytes.

BACKGROUND

More than 300 million people around the world have asthma. Despite the use of long-acting bronchodilators and inhaled corticosteroids, unscheduled visits to doctor offices, visits to emergency departments (ED), and hospitalizations due to asthma exacerbations occur frequently and account for a significant proportion of healthcare costs attributable to asthma. (Masoli M, et al. *Allergy* 59: 469-78(2004)).

Relapse following acute asthma exacerbation has been reported to range from 41 to 52% at 12 weeks despite the use of systemic steroids upon discharge (Lederle F, et al. *Arch Int Med* 147:2201-03 (1987)). Management of these patients has proved problematic due either to severe refractory disease or inability and/or unwillingness to comply with medical treatment. In one study of patients admitted to the hospital, some with near fatal asthma, 50% were non-compliant with systemic corticosteroids at 7 days following discharge (Krishnan J, et al. *AJRCCM* 170: 1281-85 (2004)). Many factors may contribute to non-compliance including poor access to routine quality healthcare (particularly in the inner city), lack of education or understanding of their disease, unwillingness to accept the chronic nature of their disease, or inability to obtain medications.

Many lines of evidence implicate eosinophils as one of the main causative cells of asthmatic airway inflammation (James A. *Curr Opin Pulm Med* 11(1):1-6 (2005)). Peripheral blood (PB) eosinophilia is a risk factor for relapse of acute asthma (Janson C and Herala M. *Resp Med* 86(2):101-104 (1992)). In subjects with peripheral blood eosinophilia, the risk of dying from asthma was 7.4 (confidence interval, 2.8-19.7) times greater than in those without eosinophilia (Ulrik C and Fredericksen J. *Chest* 108:10-15 (1995)). Necropsy results have identified 2 distinct pathogenic inflammatory mechanisms of fatal asthma (Restrepo R and Peters J. *Curr Opin Pulm Med* 14: 13-23 (2008)). A neutrophilic infiltrate is more prominent in those dying suddenly (approximately within 2 hours on onset of symptoms), while an eosinophilic infiltrate is more common in those dying from more protracted asthma crises. Sputum and blood eosinophils can also be increased in patients presenting to the ED with rapid onset of asthma symptoms (Bellido-Casado J, et al. *Arch Bronconeumol* 46(11): 587-93 (2010)). Therapies that target eosinophils lead to a reduction in the number and severity of asthma exacerbations as compared to the use of clinical guidelines (Green R, et al. *Lancet* 360: 1715-21 (2002); Haldar P, et al. *NEJM* 360:973-84 (2009)).

Benralizumab (MEDI-563) is a humanized monoclonal antibody (mAb) that binds to the alpha chain of the interleukin-5 receptor alpha (IL-5Ra), which is expressed on eosinophils and basophils. It induces apoptosis of these cells via antibody-dependent cell cytotoxicity. A single intravenous (IV) dose of benralizumab administered to adults with mild asthma provoked prolonged PB eosinopenia likely due to the effects on eosinophil/basophil bone marrow progenitors that express the target (Busse W, et al. *JACI* 125: 1237-1244 e2 (2010)). In addition, a single dose of benralizumab significantly reduced the blood eosinophil count in subjects who presented to the emergency department with a severe asthma exacerbation (WO 2013/066780). Benralizumab does not affect other cell lineages in the bone marrow or periphery. (Kolbeck R, et al. *JACI* 125:1344-53 (2010)).

Previous studies have demonstrated that an outpatient strategy focused on reducing eosinophils in the sputum reduces the number of subsequent asthma exacerbations (Green R, et al. *Lancet* 360:1715-21 (2002); Haldar P, et al. *NEJM* 360:973-84 (2009)).

Thus, given the high unmet need of reducing exacerbations of asthma and that some subjects with asthma have an eosinophilic component, the effect of benralizumab on asthma exacerbation rates in adult subjects was examined.

BRIEF SUMMARY

Methods of reducing the annual exacerbation rate of asthma are provided herein. In certain aspects, a method of reducing the annual exacerbation rate of asthma comprises administering to an asthma patient an effective amount of benralizumab or an antigen-binding fragment thereof.

Methods of treating asthma are also provided herein. In certain aspects, a method of treating asthma comprises administering to an asthma patient an effective amount of benralizumab or an antigen-binding fragment thereof, wherein the patient has a blood eosinophil count of at least 300 cells/μl prior to the administration.

In certain aspects, a method of treating asthma comprises administering to an asthma patient an effective amount of benralizumab or an antigen-binding fragment thereof, wherein the patient has a forced expiratory volume ($FEV_1$) of at least 75% predicted value prior to the administration.

In certain aspects, a method of treating asthma comprises administering at least two doses of benralizumab or an antigen-binding fragment thereof to an asthma patient.

In certain aspects of the methods provided herein, the administration reduces the patient's exacerbation rate. In certain aspects, the administration reduces the patient's annual exacerbation rate. In certain aspects, the annual exacerbations rate following administration of benralizumab or an antigen-binding fragment thereof is reduced by at least 35%. In certain aspects, the annual exacerbation rate following administration of benralizumab or an antigen-binding fragment thereof is reduced by at least 40%. In certain aspects, the annual exacerbation rate following administration of benralizumab or an antigen-binding fragment thereof is reduced by at least 50%. In certain aspects, the annual exacerbations rate following administration of benralizumab or an antigen-binding fragment thereof is reduced by at least 60%.

In certain aspects of the methods provided herein, the asthma is eosinophilic asthma. In certain aspects, the patient has a blood eosinophil count of at least 300 cells/μl.

In certain aspects of the methods provided herein, the patient has a forced expiratory volume ($FEV_1$) of at least 75% predicted value prior to the administration. In certain aspects, the patient has an asthma control questionnaire score of at least 1.5 prior to the administration. In certain aspects, the patient uses high-dose inhaled corticosteroids (ICS). In certain aspects, the patient uses long-acting β2 agonists (LABA). In certain aspects, the patient has a history of exacerbations. In certain aspects, the history of exacerbations comprises at least two exacerbations in the year prior to the administration of benralizumab or an antigen-binding fragment thereof. In certain aspects, the history of exacerbations comprises no more than six exacerbations in the year prior to the administration of benralizumab or an antigen-binding fragment thereof In certain aspects of the methods provided herein, at least two doses of benralizumab or an antigen-binding fragment thereof are administered to the patient.

In certain aspects of the methods provided herein, benralizumab or an antigen-binding fragment thereof is administered at about 2 mg to about 100 mg per dose. In certain aspects, benralizumab or an antigen-binding fragment thereof is administered at about 20 mg per dose. In certain aspects, benralizumab or an antigen-binding fragment thereof is administered at about 30 mg per dose. In certain aspects, benralizumab or an antigen-binding fragment thereof is administered at about 100 mg per dose.

In certain aspects of the methods provided herein, benralizumab or an antigen-binding fragment thereof is administered once every four weeks to once every twelve weeks. In certain aspects, the benralizumab or antigen-binding fragment thereof is administered once every four weeks. In certain aspects, benralizumab or an antigen-binding fragment thereof is administered once every eight weeks. In certain aspects, benralizumab or an antigen-binding fragment thereof is administered once every four weeks for twelve weeks and then once every eight weeks.

In certain aspects of the methods provided herein, benralizumab or an antigen-binding fragment thereof is administered parenterally. In certain aspects, benralizumab or an antigen-binding fragment thereof is administered subcutaneously.

In certain aspects of the methods provided herein, benralizumab or an antigen-binding fragment thereof is administered in addition to corticosteroid therapy.

In certain aspects, a method of reducing the annual exacerbation rate of asthma comprises administering to an asthma patient 20-100 mg of benralizumab or an antigen-binding fragment thereof, wherein the patient has an blood eosinophil count of at least 300 cells/µl prior to the administration. In certain aspects, the method comprises administering 20 mg of benralizumab or an antigen-binding fragment thereof. In certain aspects, the 20 mg of benralizumab is administered once every four weeks for twelve weeks and then once every eight weeks. In certain aspects, the method comprises administering 30 mg of benralizumab or an antigen-binding fragment thereof. In certain aspects, the 30 mg of benralizumab is administered once every four weeks for eight weeks and then once every eight weeks. In certain aspects, the 30 mg of benralizumab is administered once every four weeks. In certain aspects, the method comprises administering 100 mg of benralizumab or an antigen-binding fragment thereof. In certain aspects, the 100 mg of benralizumab is administered once every four weeks for twelve weeks and then once every eight weeks.

In certain aspects, a method of treating asthma in an asthma patient comprises administering to the patient a dose of at least 2 and less than 100 mg of benralizumab or an antigen-binding fragment thereof. In certain aspects, the method comprises administering 20 mg of benralizumab or an antigen-binding fragment. In certain aspects, the method comprises administering 30 mg of benralizumab or an antigen-binding fragment. In certain aspects, the method comprises administering a dose of at least 20 and less than 100 mg of benralizumab or an antigen-binding fragment. In certain aspects, the method comprises administering a dose of at least 30 and less than 100 mg of benralizumab or an antigen-binding fragment. In certain aspects, the method decreases exacerbation rates of asthma. In certain aspects, the method decreases annual exacerbation rates of asthma. In certain aspects, the administration is subcutaneous.

In certain aspects of the provided methods, administration of benralizumab or an antigen-binding fragment thereof results in the reduction in exacerbation rates as shown in FIGS. 2-8.

In certain aspects of the provided methods, administration of benralizumab or an antigen-binding fragment thereof results in the reduction in exacerbation rates as shown in Examples 1-2.

BRIEF DESCRIPTION OF THE DRAWINGS/FIGURES

FIG. 2 shows the interim (24 weeks) and annual (Stage I; 52 weeks) exacerbation rates after treatment with placebo, 2 mg benralizumab, 20 mg benralizumab, or 100 mg benralizumab in patients with fewer than 300 eosinophils/µl and patients with at least 300 eosinophils/µl.

FIG. 3 shows the interim (24 weeks) and annual (Stage I; 52 weeks) exacerbation rates after treatment with placebo, 2 mg benralizumab, 20 mg benralizumab, or 100 mg benralizumab in patients with medium or high use of inhaled corticosteroids (ICS).

FIG. 4 shows the interim (24 weeks) and annual (Stage I; 52 weeks) exacerbation rates after treatment with placebo, 2 mg benralizumab, 20 mg benralizumab, or 100 mg benralizumab in patients with fewer than 300 eosinophils/µl and (i) medium use of ICS or (ii) high use of ICS.

FIG. 5 shows the interim (24 weeks) and annual (Stage I; 52 weeks) exacerbation rates after treatment with placebo, 2 mg benralizumab, 20 mg benralizumab, or 100 mg benralizumab in patients with at least 300 eosinophils/µl and (i) medium use of ICS or (ii) high use of ICS.

FIGS. 7A and 7B show the number of exacerbations in patients with various eosinophil counts.

DETAILED DESCRIPTION

Figure 1:
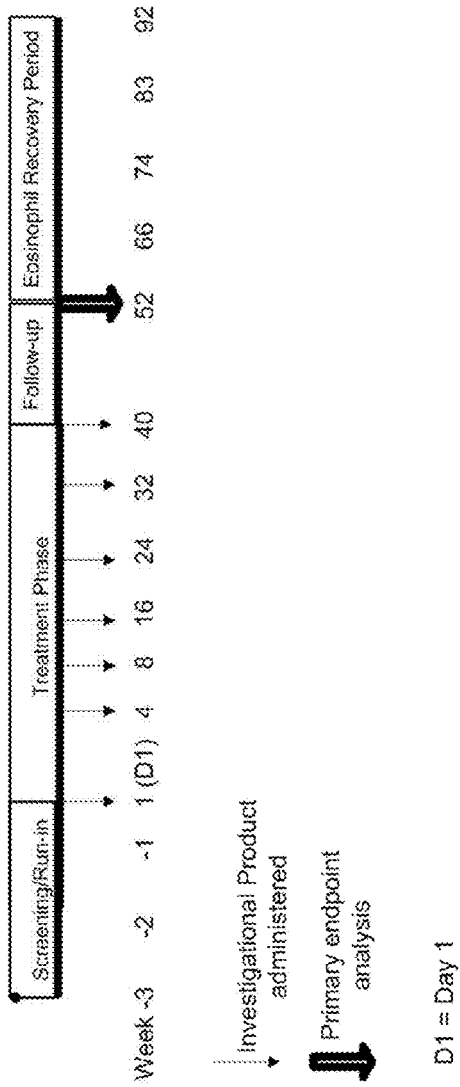
FIG. 1 shows the study flow diagram.

It is to be noted that the term "a" or "an" entity refers to one or more of that entity; for example, "an anti-IL-5α antibody" is understood to represent one or more anti-IL-5α antibodies. As such, the terms "a" (or "an"), "one or more," and "at least one" can be used interchangeably herein.

Provided herein are methods for reducing exacerbations of asthma. The methods provided include administering an effective amount of benralizumab or an antigen-binding fragment thereof.

Information regarding benralizumab (or fragments thereof) for use in the methods provided herein can be found in U.S. Patent Application Publication No. US 2010/0291073 A1, the disclosure of which is incorporated herein by reference in its entirety. Benralizumab and antigen-binding fragments thereof for use in the methods provided herein comprise a heavy chain and a light chain or a heavy chain variable region and a light chain variable region. In a further aspect, benralizumab or an antigen-binding fragment thereof for use in the methods provided herein includes any one of the amino acid sequences of SEQ ID NOs: 1-4. In a specific aspect, benralizumab or an antigen-binding fragment thereof for use in the methods provided herein comprises a light chain variable region comprising the amino acid sequence of SEQ ID NO:1 and a heavy chain variable region comprising the amino acid sequence of SEQ ID NO:3. In a specific aspect, benralizumab or an antigen-binding fragment thereof for use in the methods provided herein comprises a light chain comprising the amino acid sequence of SEQ ID NO: 2 and heavy chain comprising the amino acid sequence of SEQ ID NO:4. In a specific aspect, benralizumab or an antigen-binding fragment thereof for use in the methods provided herein comprises a heavy chain variable region and a light chain variable region, wherein the heavy chain variable region comprises the Kabat-defined CDR1, CDR2, and CDR3 sequences of SEQ ID NOs: 7-9, and wherein the light chain variable region comprises the Kabat-defined CDR1, CDR2, and CDR3 sequences of SEQ ID NOs: 10-12. Those of ordinary skill in the art would easily be able to identify Chothia-defined, Abm-defined or other CDRs. In a specific aspect, benralizumab or an antigen-binding fragment thereof for use in the methods provided herein comprises the variable heavy chain and variable light chain CDR sequences of the KM1259 antibody as disclosed in U.S. Pat. No. 6,018,032, which is herein incorporated by reference in its entirety.

In certain aspects, a patient presenting at a physician's office or ED with asthma is administered benralizumab or an antigen-binding fragment thereof. Given the ability benralizumab to reduce or deplete eosinophil counts for up to 12 weeks or more (see US 2010/0291073), benralizumab or an antigen-binding fragment thereof can be administered only once or infrequently while still providing benefit to the patient in reducing exacerbations. In further aspects the patient is administered additional follow-on doses. Follow-on doses can be administered at various time intervals depending on the patient's age, weight, ability to comply with physician instructions, clinical assessment, eosinophil count (blood or sputum eosinophils), Eosinophilic Cationic Protein (ECP) measurement, Eosinophil-derived neurotoxin measurement (EDN), Major Basic Protein (MBP) measurement and other factors, including the judgment of the attending physician. The intervals between doses can be every 4 weeks, every 5 weeks, every 6 weeks, every 8 weeks, every 10 weeks, every 12 weeks, or longer intervals. In certain aspects the intervals between doses can be every 4 weeks, every 8 weeks, or every 12 weeks. In certain aspects, the single dose or first dose is administered to the asthma patient shortly after the patient presents with an exacerbation, e.g., a mild, moderate or severe exacerbation. For example, benralizumab or an antigen-binding fragment thereof can be administered during a presenting clinic or hospital visit, or in the case of very severe exacerbations, within 1, 2, 3, 4, 5, 6, 7, or more days, e.g., 7 days of the acute exacerbation, allowing the patient's symptoms to stabilize prior to administration of benralizumab.

In some embodiments, at least two doses of benralizumab or an antigen-binding fragment thereof are administered to the patient. In some embodiments, at least three doses, at least four doses, at least five doses, at least six doses, or at least seven doses are administered to the patient. In some embodiments, benralizumab or an antigen-binding fragment thereof is administered over the course of four weeks, over the course of eight weeks, over the course of twelve weeks, over the course of twenty-four weeks, or over the course of a year.

The amount of benralizumab or antigen-binding fragment thereof to be administered to the patient will depend on various parameters such as the patient's age, weight, clinical assessment, eosinophil count (blood or sputum eosinophils), Eosinophilic Cationic Protein (ECP) measurement, Eosinophil-derived neurotoxin measurement (EDN), Major Basic Protein (MBP) measurement and other factors, including the judgment of the attending physician. In certain aspects, the dosage or dosage interval is not dependent on the eosinophil level.

In certain aspects the patient is administered one or more doses of benralizumab or an antigen-binding fragment thereof, wherein the dose is about 2 mg to about 100 mg, for example about 20 mg to about 100 mg, or about 30 mg to about 100 mg. In certain specific aspects, the patient is administered one or more doses of benralizumab or an antigen-binding fragment thereof where the dose is about 20 mg, about 30 mg, about 40 mg, about 50 mg, about 60 mg, about 70 mg, about 80 mg, about 90 mg, or about 100 mg. In some embodiments, the dose is about 20 mg. In some embodiments the dose is about 30 mg. In some embodiments, the dose is about 100 mg.

In certain aspects, administration of benralizumab or an antigen-binding fragment thereof according to the methods provided herein is through parenteral administration. For example, benralizumab or an antigen-binding fragment thereof can be administered by intravenous infusion or by subcutaneous injection.

In certain aspects, benralizumab or an antigen-binding fragment thereof is administered according to the methods provided herein in combination or in conjunction with additional asthma therapies. Such therapies include, without limitation, inhaled corticosteroid therapy, long- or short-term bronchodilator treatment, oxygen supplementation, or other standard therapies as described, e.g., in the National Asthma Education and Prevention Program (NAEPP) Guidelines. In certain aspects, use of the methods provided herein, i.e., administration of benralizumab or an antigen-binding fragment thereof to an asthma patient with a history of exacerbations serves as adjunct therapy in situations of poor compliance with standard forms of asthma management.

The methods provided herein can significantly reduce exacerbations of asthma. Reduction can be measured based on the expected exacerbations predicted based on a large patient population, or based on the individual patient's history of exacerbations. In certain aspects, the patient population is those patients who had ≥2 exacerbations requiring systemic corticosteroid bursts in the past year. In certain aspects, the patient population is those patients who had ≥2 exacerbations requiring systemic corticosteroid bursts in the past year and ≤6 exacerbations requiring systemic corticosteroid bursts in the past year. In certain aspects, the patient population is patients having an eosinophil count of at least 300 cells/μl.

In certain aspects, use of the methods provided herein, i.e., administration of benralizumab or an antigen-binding fragment thereof reduces the number of exacerbations experienced by the patient over a 24-week period following administration of benralizumab or an antigen-binding fragment thereof, as compared to the number of exacerbations expected according to the patient's history, as compared to the average number of exacerbations expected in a comparable population of patients, or as compared to a comparable population treated with placebo over the same time period. In certain aspects, the patient can receive follow on doses of benralizumab or an antigen-binding fragment thereof at periodic intervals, e.g., every 4 weeks, every 5 weeks, every 6 weeks, every 8 weeks, every 12 weeks, or as scheduled based on patient's age, weight, ability to comply with physician instructions, clinical assessment, eosinophil count (blood or sputum eosinophils), Eosinophilic Cationic Protein (ECP) measurement, Eosinophil-derived neurotoxin measurement (EDN), Major Basic Protein (MBP) measurement and other factors, including the judgment of the attending physician. Use of the methods provided herein can reduce the frequency of exacerbations by 10%, 20%, 30%, 35%, 40%, 45%, 50%, 55%, 60%, 65%, 70%, 75%, 80%, 85%, 90%, 95% or 100% over the 24-week period.

In other aspects, use of the methods provided herein, i.e., administration of benralizumab or an antigen-binding fragment thereof to an asthma patient, reduces the number of exacerbations experienced by the patient over a 52-week period (i.e., the annual exacerbation rate) following administration of benralizumab or an antigen-binding fragment thereof, as compared to the number of exacerbations expected according to the patient's history, as compared to the average number of exacerbations expected in a comparable population of patients, or as compared to a comparable population treated with placebo over the same time period. In certain aspects, the patient can receive follow on doses of benralizumab or an antigen-binding fragment thereof at periodic intervals, e.g., every 4 weeks, every 5 weeks, every 6 weeks, every 8 weeks, every 12 weeks, or as scheduled based on patient's age, weight, ability to comply with physician instructions, clinical assessment, eosinophil count (blood or sputum eosinophils), Eosinophilic Cationic Protein (ECP) measurement, Eosinophil-derived neurotoxin measurement (EDN), Major Basic Protein (MBP) measurement and other factors, including the judgment of the attending physician. In certain aspects, the interval is every 4 weeks, every 8 weeks or every 12 weeks. Use of the methods provided herein can reduce the annual exacerbations by 10%, 20%, 30%, 35%, 40%, 45%, 50%, 55%, 60%, 65%, 70%, 75%, 80%, 85%, 90%, 95% or 100%.

In certain aspects, use of the methods provided herein, i.e., administration of benralizumab or an antigen-binding fragment thereof to an asthma patient, reduces the annual exacerbation rate, increases forced expiratory volume ($FEV_1$), and/or improves an asthma questionnaire score (e.g., the asthma control questionnaire (ACQ)).

In certain aspects, the patient is "eosinophilic positive" meaning the patient is one whose asthma is likely to be eosinophilic.

In certain aspects, the asthma patient has a particular blood eosinophil count, e.g., prior to the administration of benralizumab or an antigen-binding fragment thereof. Blood eosinophil counts can be measured, for example, using a complete blood count (CBC) with cell differential.

In certain aspects, the asthma patient has a blood eosinophil count of at least 300 cells/µl prior to the administration of benralizumab or an antigen-binding fragment thereof. In certain aspects, the asthma patient has a blood eosinophil count of at least 350 cells/µl, at least 400 cells/µl, at least 450 cells/µl, or at least 500 cells/µl prior to the administration of benralizumab or an antigen-binding fragment thereof.

In certain aspects, the asthma patient has a blood eosinophil count of less than 300 cells/µl prior to the administration of benralizumab or an antigen-binding fragment thereof. In certain aspects, the asthma patient has a blood eosinophil count of at least 100 cells/µl, at least 150 cells/µl, at least 180 cells/µl, at least 200 cells/µl, or at least 250 cells/µl prior to the administration of benralizumab or an antigen-binding fragment thereof.

In certain aspects, the asthma patient was prescribed or has been using a medium-dose of inhaled corticosteroids (ICS) use prior to the administration of benralizumab or an antigen-binding fragment thereof. A medium-dose of ICS can be a dose of at least 600 µg to 1,200 µg budesonide daily or an equivalent dose of another ICS.

In certain aspects, the asthma patient was prescribed or had been using a high-dose of ICS use prior to the administration of benralizumab or an antigen-binding fragment thereof. A high-dose of ICS can be a dose of at least 1,200 µg budesonide daily or an equivalent dose of another ICS. A high dose of ICS can also be a dose of greater than 1,200 µg to 2000 µg budesonide daily or an equivalent dose of another ICS.

In certain aspects, the asthma patient was prescribed or has been using oral corticosteroids prior to the administration of benralizumab or an antigen-binding fragment thereof. In certain aspects, administration of benralizumab or an antigen-binding fragment thereof decreases the use of oral corticosteroids in an asthma patient. In certain aspects, the administration decreases the use of oral corticosteroids in an asthma patient by at least 50%.

In certain aspects, the asthma patient was prescribed or had been using a long-acting beta agonist (LABA) prior to the administration of benralizumab or an antigen-binding fragment thereof.

In certain aspects, the asthma patient was prescribed or had been using both ICS and LABA prior to the administration of benralizumab or an antigen-binding fragment thereof.

In certain aspects, the asthma patient has a blood eosinophil count of at least 300 cells/µl and high ICS use prior to the administration of benralizumab or an antigen-binding fragment thereof.

In certain aspects, the asthma patient had a forced expiratory volume in 1 second ($FEV_1$) of at least 40% and less than 90% predicted value prior to the administration of benralizumab or an antigen-binding fragment thereof. In some embodiments, the $FEV_1$ was greater than 70% predicted value prior to the administration of benralizumab or an antigen-binding fragment thereof. In some embodiments, the $FEV_1$ was greater than 70% and less than 90% predicted value prior to the administration of benralizumab or an antigen-binding fragment thereof. In some embodiments, the $FEV_1$ was at least 75% predicted value prior to the administration of benralizumab or an antigen-binding fragment thereof. In some embodiments, the $FEV_1$ was at least 75% and less than 90% prior predicted value to the administration of benralizumab or an antigen-binding fragment thereof. In some embodiments, the $FEV_1$ was at least 80% predicted value prior to the administration of benralizumab or an antigen-binding fragment thereof. In some embodiments, the $FEV_1$ was at least 80% and less than 90% predicted value prior to the administration of benralizumab or an antigen-binding fragment thereof.

EXAMPLES

Example 1

Patients and Methods

Subjects

Subjects in this study were required to be 18 to 75 years of age with a weight of greater than 45 kg and less than or equal to 150 kg (greater than 100 pounds, but less than or equal to 330 pounds). They also must have had a physician diagnosis of asthma for a minimum of 12 months prior to screening as well as physician prescribed daily use of medium-dose or high-dose inhaled corticosteroids (ICS) plus long-acting beta agonist (LABA) or any combination of sequential dosing of either medium-dose or high-dose ICS/LABA for at least 12 months prior to screening. Medium and high-doses of ICS as defined in this study are shown in Table 1 below.

TABLE 1

Estimated Comparative Daily Dosages for Inhaled Corticosteroids

| Drug | Medium Daily Dose (Adult) | High Daily Dose (Adult) |
|---|---|---|
| Beclamethazone HFA/MDI | | |
| 40 or 80 µg/puff | >240-480 µg | >480 µg |
| Budesonide DPI | | |
| 90, 180, or 200 µg/inhalation | >600-1,200 µg | >1,200 µg |
| Ciclesonide HFA/MDI | | |
| 80 or 160 µg/inhalation | >160-320 µg | >320-1280 µg |
| Flunisolide CFC/MDI | | |
| 250 µg/puff | >1,000-2,000 µg | >2,000 µg |
| Flunisolide HFA/MDI | | |
| 80 µg/puff | >320-640 µg | >640 µg |
| Fluticasone | | |
| HFA/MDI: 44, 110, or 220 µg/puff | >264-440 µg | >440 µg |
| DPI: 50, 100, or 250 µg/puff | >300-500 µg | >500 µg |
| Mometasone DPI | | |
| 200 µg/inhalation | 400 µg | >400 µg |
| Triamcinolone acetonide CFC/MDI | | |
| 75 µg/puff | >750-1,500 µg | >1,500 µg |

CFC = chlorofluorocarbon; DPI = dry powder inhaler; HFA = hydrofluoroalkane; MDI = metered dose inhaler.

The dose of other asthma controller medications must have been stable in the subjects for at least 30 days prior to screening. Subjects must also have had at least 2, but no more than 6, documented asthma exacerbations in the 12 months prior to screening that required the use of a systemic corticosteroid burst. Subjects must also have had a morning pre-bronchodilator forced expiratory volume in 1 second ($FEV_1$) of at least 40% and less than 90% predicted during the screening/run-in period (described below). Subjects must also have fulfilled one of the following criteria:

(a) Proof of post-bronchodilator reversibility of airflow obstruction ≥12% and ≥200 mL documented within 36 months prior to randomization or proof of a positive response [PC20≤8 mg/mL] to a methacholine challenge documented within 36 months prior to randomization; OR
(b) A post-bronchodilator increase in $FEV_1$≥12% and ≥200 mL at Week −3 screening visit; OR
(c) If a) and b) were not met and all other inclusion/exclusion criteria were met, subjects with a $FEV_1$ of ≥1.5 L and ≥60% predicted on the Week −2 screening visit were eligible to undergo a methacholine challenge at the Week-2 screening visit at sites where methacholine testing was available. If the subject achieved a positive response, (PC20≤8 mg/mL), then this inclusion criterion was met.

Subjects must also have had an Asthma Control Questionnaire (ACQ) score of at least 1.5 at least twice during the screening/run-in period.

Subjects were not able to participate if they had a cigarette exposure of 10 pack-years or more or had been smoking within 12 months prior to screening or had any condition (e.g., any eosinophilic lower respiratory disease other than asthma, chronic obstructive pulmonary disease (COPD), or cystic fibrosis) that, in the opinion of the investigator or medical monitor, would interfere with the evaluation. Subjects were also not able to participate if they had received an oral corticosteroid burst or short-acting systemic corticosteroid within 30 days prior to screening or during the screening/run-in period.

Design of the Study

The study was a phase 2b randomized, double-blind, placebo-controlled, dose-ranging, multicenter study (ClinicalTrials.gov number: NCT01238861) in which multiple doses of benralizumab were administered subcutaneously to asthma patients. Benralizumab was administered at 2, 20, or 100 mg doses, and patients were followed for 1 year. The study flow diagram is shown in FIG. 1.

A 3-week screening/run-in period preceded administration of benralizumab or placebo. During the 3-week period, subjects continued to use the same medium-dose or high-dose ICS/LABA combination product as prior to the participation in the study (doses of ICS/LABA were required to be stable for 30 days prior to the 3-week screening/run-in period). Subjects remained on the same dose of ICS/LABA throughout the study.

The administered benralizumab composition contained benralizumab (50 mg/mL), 10 mM histidine, 10 mM histidine HCl monohydrate, 9% (w/v) trehalose dihydrate, and 0.004% (w/v) polysorbate-20, pH 6. The administered placebo composition contained 10 mM histidine, 10 mM histidine hydrochloride monohydrate, 9% (w/v) trehalose dihydrate, and 0.02% (w/v) polysorbate-20, pH 6.

Subjects received two subcutaneous (SC) injections of 1 ml of benralizumab or placebo every four weeks for the first 3 doses on Weeks 1 (Day 1), 4, and 8 and then every 8 weeks thereafter for the last 4 doses on Weeks 16, 24, 32, and 40. After Week 40, subjects were followed for an additional 12 weeks (through Week 52) for assessment of acute exacerbations. The day of receipt of the first dose of benralizumab or placebo was considered Day 1.

For the purpose of this study, an asthma exacerbation was defined as a progressive increase of asthma symptoms (cough, wheeze, chest tightness, and/or shortness of breath) that did not resolve after the initiation of rescue medications and remained troublesome for the subject resulting in either 1) use of systemic corticosteroids (tablets, suspension or injection) or increase of a stable systemic maintenance dose for a duration of at least 3 days as prescribed or administered by the investigator or healthcare provider; or 2) subject initiation of systemic corticosteroids for a duration of at least 3 days. An asthma exacerbation event was considered resolved 7 days after the last dose of oral corticosteroid was administered (10 days after administration of an injectable corticosteroid). Courses of corticosteroids initiated after this time period were considered a separate new asthma exacerbation. Asthma exacerbations were classified as "moderate" if worsening symptoms required systemic corticosteroids or "severe" if worsening symptoms required systemic corticosteroids and urgent care evaluation and/or hospital admission.

Asthma exacerbations were assessed at weeks −3, −2, −1, 1 (on Day 1 and Day 6), 4, 8, 12, 16, 20, 24, 28, 32, 36, 40, 46, and 52.

Annual exacerbation rate was defined as the number of exacerbations from Week 1 (Day 1) to Week 52. If a subject discontinued before the Week 52 visit, the annual exacerbation rate for that subject was calculated according to the following formula: observed number of asthma exacerbations/observed Days×364.

Weighted mean rate of asthma exacerbations was estimated by pooling all the asthma exacerbations in a treatment group and dividing by the total follow-up time in that treatment group.

Safety Assessments

Adverse events were monitored following administration of placebo or benralizumab. Other assessments included physical examination, vital sign monitoring, and laboratory measurements.

Example 2

Results

Enrollment and Baseline Characteristics

The baseline characteristics of all randomized subjects who received any dose of investigational product are provided in Table 2 below. The mean population ICS dose was 1100 budesonide equivalents overall, 700 budesonide equivalents in the medium dose stratum, and 1600 budesonide equivalents in the high dose stratum.

TABLE 2

Demographics for Baseline Eosinophils (EOS)

| POPULATION | PLACEBO EOS < 300 | BENRALIZUMAB EOS < 300 | PLACEBO EOS >= 300 | BENRALIZUMAB EOS >= 300 |
|---|---|---|---|---|
| N | 139 | 151 | 83 | 232 |
| Mean Age (yrs) | 50.3 | 51.2 | 45.2 | 46.3 |
| Gender Female (%) | 71 | 70 | 66 | 68 |
| Race White (%) | 76 | 80 | 64 | 65 |
| BMI (mean) | 29.6 | 29.2 | 28.8 | 28.5 |
| EOS mean cells/μl | 149 | 156 | 542 | 548-615 |
| Chronic OCS (%) | 2.2% | 7.9% | 4.8% | 4.3% |
| $FEV_1$ (L) % pred | 70.0 | 54-69 | 65 | 64-67 |
| Reversibility (%) | 12.5 | 13-18 | 15.5 | 17-19 |
| Historical Exacerbations | 2.2 | 2.3-2.5 | 2.2 | 2.3-2.5 |
| ACQ at Baseline | 2.5 | 2.5-2.8 | 2.6 | 2.4-2.7 |
| Childhood Asthma YES | 32% | 33-38% | 40% | 37-41% |
| History Nasal Polyps YES | 10.8% | 11.9% | 14.5% | 19.3% |
| $FE_{NO}$ mean ppb | 22.1 | 21-39 | 34.8 | 34-42 |

OCS = oral corticosteroids; $FEV_1$ = forced expiratory volume in 1 second; ACQ = asthma control questionnaire; and FENO = fraction of exhaled nitric oxide.

The baseline characteristics of randomized subjects who received any dose of investigational product and had a baseline eosinophil count of at least 300 cells/μl are shown in Table 3 below.

TABLE 3

Demographics for ICS with Baseline EOS at Least 300 Cells/μl

| POPULATION | PLACEBO MED ICS | BENRALIZUMAB MED ICS | PLACEBO HIGH ICS | BENRALIZUMAB HIGH ICS |
|---|---|---|---|---|
| N | 43 | 121 | 40 | 111 |
| Mean Age (yrs) | 45 | 46-47 | 45 | 45-47 |
| Gender Female (%) | 65 | 63 | 68 | 70-79 |
| Race White (%) | 56 | 66 | 73 | 63 |
| BMI (mean) | 27.3 | 27.6-28.3 | 30.3 | 27.8-30.0 |
| EOS mean cells/μl | 480 | 462-625 | 608 | 605-656 |
| Chronic OCS (%) | 0 | 0 | 10% | 9% |
| $FEV_1$ (L) % pred | 68.8 | 64-70 | 60 | 63-65 |
| Reversibility (%) | 16% | 17-23% | 15% | 14-21% |
| Historical Exacerbations | 2.2 | 2.1-2.5 | 2.3 | 2.4-2.5 |
| ACQ at Baseline | 2.6 | 2.3-2.6 | 2.7 | 2.6-2.8 |
| Childhood Asthma YES | 42% | 36% | 38% | 27-53% |

TABLE 3-continued

Demographics for ICS with Baseline EOS at Least 300 Cells/μl

| POPULATION | PLACEBO MED ICS | BENRALIZUMAB MED ICS | PLACEBO HIGH ICS | BENRALIZUMAB HIGH ICS |
|---|---|---|---|---|
| History Nasal Polyps YES | 14% | 11% | 15% | 23-37% |
| $FE_{NO}$ mean ppb | 38.3 | 35-45 | 31.0 | 33-39 |

OCS = oral corticosteroids; $FEV_1$ = forced expiratory volume in 1 second; ACQ = asthma control questionnaire; and FENO = fraction of exhaled nitric oxide.

Efficacy

The effects of administration of benralizumab on exacerbation rates are shown in FIGS. 2-8. Only about 30% of the subjects had exacerbations. In addition, administration of 20 mg or 100 mg of benralizumab significantly reduced (p<0.169) annual exacerbation rates in asthma patients with a blood eosinophil count of at least 300 cells/μl and in asthma patients with both a blood eosinophil count of at least 300 cells/pi and a high baseline ICS status.

In patients with a blood eosinophil count of at least 300 cells/μl, administration of 20 mg of benralizumab reduced the annual exacerbation rate by 57% (p=0.014), and administration of 100 mg of benralizumab reduced the annual exacerbation rate by 43% (p=0.049) compared to treatment with placebo (FIG. 2).

In patients with a blood eosinophil count of at least 300 cells/μl and a high baseline ICS status, administration of 20 mg of benralizumab reduced the annual exacerbation rate by 52% (p=0.118), and administration of 100 mg of benralizumab reduced the annual exacerbation rate by 46% (p=0.102) compared to treatment with placebo (FIG. 5).

Reductions in exacerbation rates were also observed in patients with a blood eosinophil count of less than 300 cells/μl (FIGS. 2 and 4) as well as patients with a medium or high baseline ICS (FIG. 3).

Figure 6:
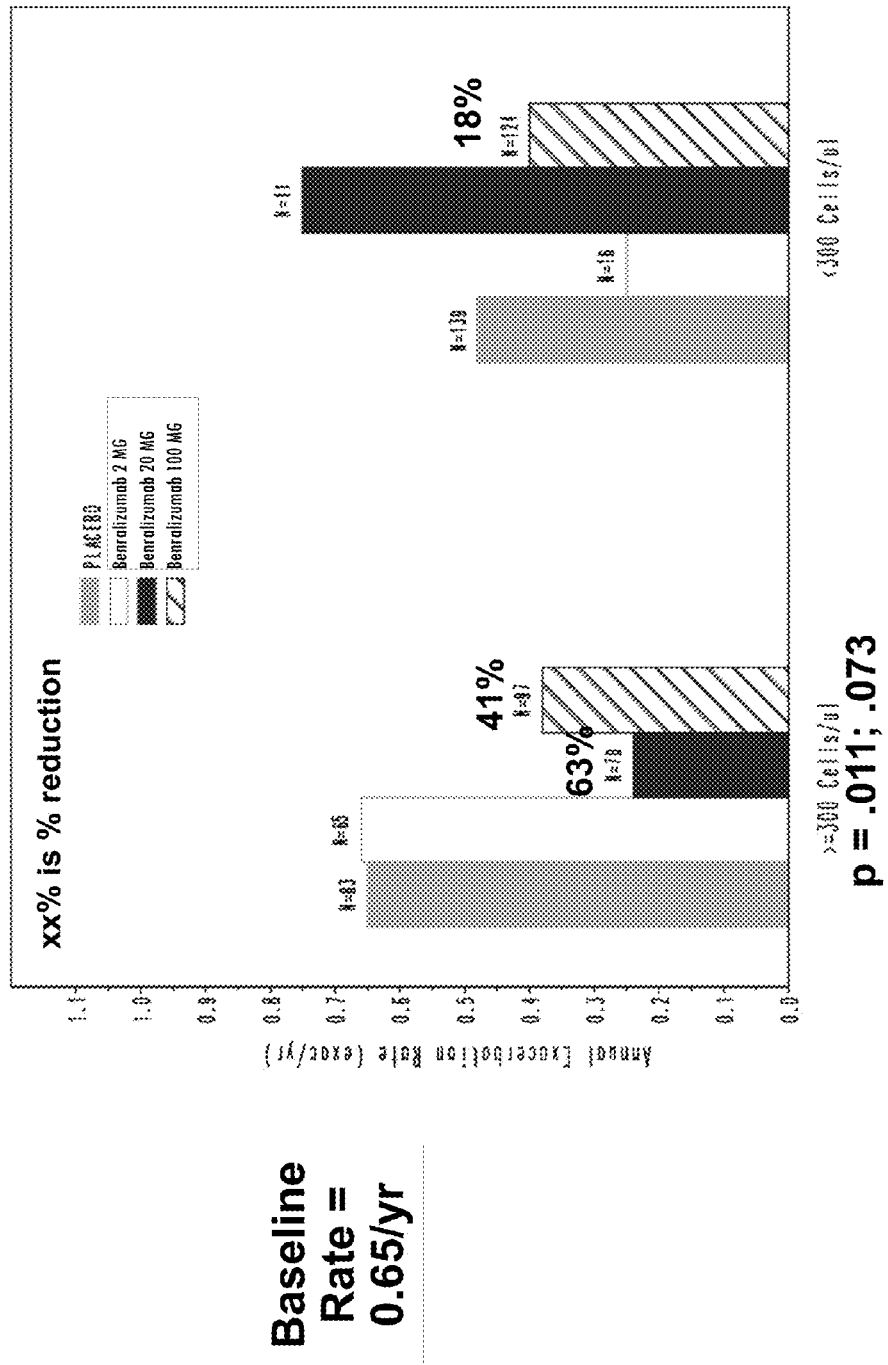
FIG. 6 shows the annual exacerbation rates in patients with fewer than 300 eosinophils/µl and patients with at least 300 eosinophils/µl.

A comparison of the reduction in exacerbation rates in patients with less than 300 cells/μl and patients with at least 300 cells/μl prior to treatment is shown in FIG. 6, and the number of exacerbations at various eosinophil counts are provided in FIG. 7.

Figure 8:
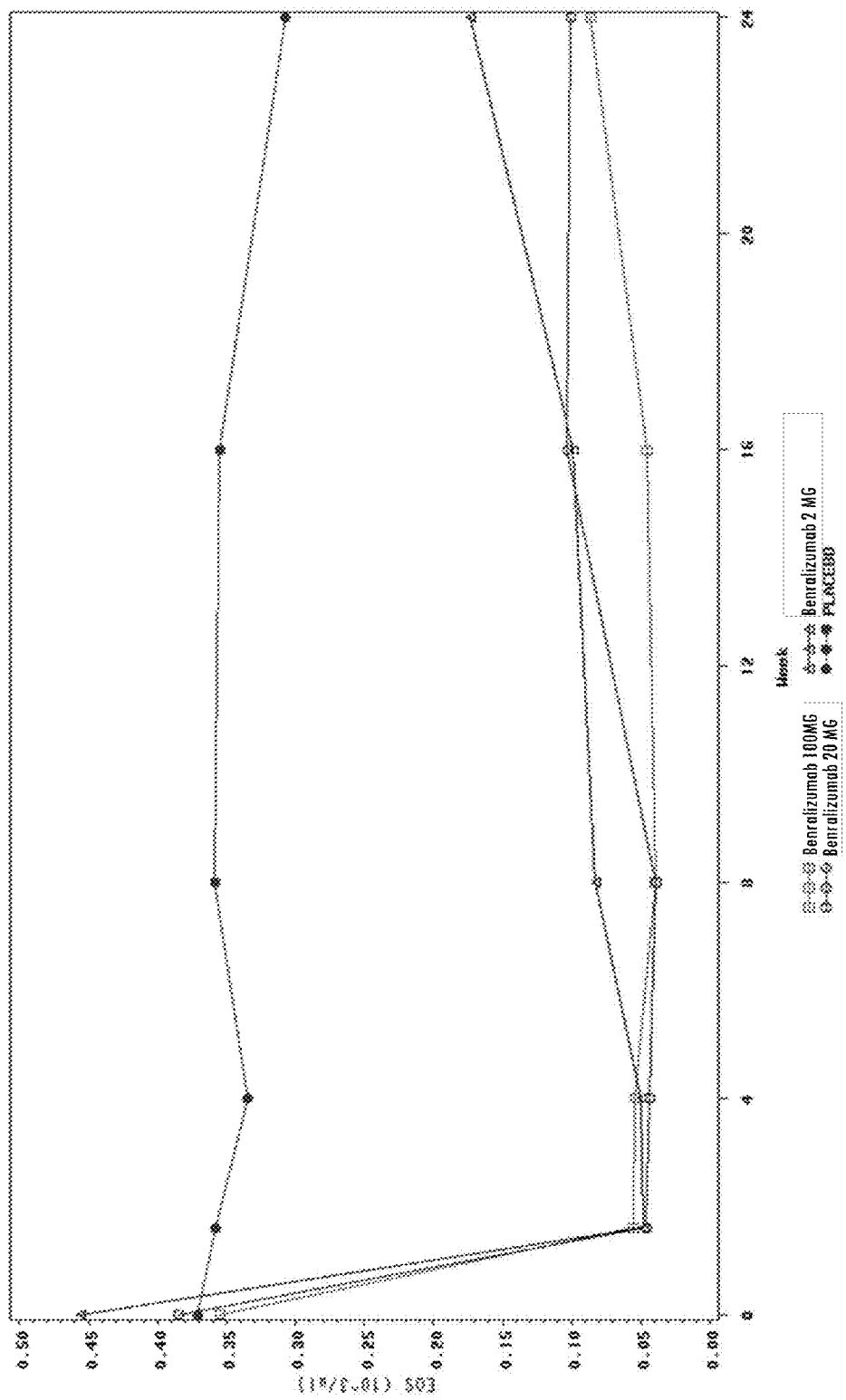
FIG. 8 shows the time course of eosinophil depletion in patients with at least 300 eosinophils/µl.

In addition, eosinophils were reduced in patients receiving any dose of benralizumab as compared to patients receiving placebo. FIG. 8.

Safety

Treatment emergent adverse events (TEAEs) occurred at an approximate 10 percentage point higher frequency in patients treated with benralizumab compared with those treated with placebo. Treatment emergent severe adverse events (TE-SAES) occurred at similar frequencies in patients treated with benralizumab and placebo. TEAEs and TE-SAEs were not dose dependent in patients treated with benralizumab.

Anti-Drug Antibodies

The development of anti-drug antibodies (ADA) to benralizumab was inversely related to dose, with the highest proportion of ADA-positive subjects at the 2 mg dose (see Table 4 below). The incidence of high titer ADA (≥400) was 12% and 9% in the 20 and 100 mg dose groups, respectively. High titer ADAs were associated with reduced benralizumab concentration and varying degrees of eosinophil recovery when present. The pharmacokinetic/pharmacodynamic (PK/PD) impact of high titer ADA was reduced at higher drug exposures. No pattern was observed between TEAEs and ADA.

TABLE 4

Anti-Drug Antibodies at Week 24

| Treatment Group | Total Number of Subjects | % Subjects with Positive ADA Titres | % Subjects with ADA Titres ≥ 400 |
|---|---|---|---|
| Placebo | 222 | 8.1% (n = 18) | 3% (n = 6) |
| Benralizumab 2 mg | 81 | 34.6% (n = 28) | 23% (n = 19) |
| Benralizumab 20 mg | 81 | 18.5% (n = 15) | 12% (n = 10) |
| Benralizumab 100 mg | 222 | 21.2% (n = 47) | 9% (n = 20) |

Based on both PK and immunological considerations, additional patients will receive dosing of 30 mg benralizumab. In some patients, the 30 mg benralizumab dose will be administered every four weeks. In some patients, the 30 mg benralizumab dose will be administered once every four weeks for three doses and then once every eight weeks thereafter.

Discussion

This study demonstrates that benralizumab reduced exacerbations in eosinophilic asthma patients (i.e., patients with a baseline blood eosinophil count of at least 300 cells/μl) on medium or high-dose ICS/LABA. In particular, benralizumab significantly reduced exacerbation rates in asthma patients with blood eosinophil counts of at least 300 cells/μl as well as patients with both a blood eosinophil counts of at least 300 cells/μl and a high ICS status. In these patients, exacerbation rates were reduced at both interim (24-week) and annual (52-week) time points and in patients receiving either 20 mg or 100 mg of benralizumab.

Example 3

Additional Dose Evaluation

Dose-efficacy modeling was performed to identify additional doses of benralizumab that reduce annual exacerbation rates and are safe and well tolerated. The modeling indicated that a dose of about 30 mg is the minimum effective dose to produce 90% maximum treatment effect. Therefore patients with uncontrolled asthma receive subcutaneous injections of 30 mg of benralizumab or placebo. The 30 mg doses are administered (i) every four weeks or (ii) every four weeks for eight weeks (3 doses) and then every eight weeks (i.e., every 8 weeks including an additional dose at week 4). The number of exacerbations in patients receiving 30 mg benralizumab is compared to the number of exacerbations in patients receiving placebo in order to demonstrate that 30 mg doses of benralizumab decrease annual exacerbation rates. In addition, the number of exacerbations in patients with baseline blood eosinophil count of at least 300 cells/μl is analyzed in order to demonstrate that 30 mg doses of benralizumab can be effective in decrease annual exacerbation rates in such patients.

Those skilled in the art will recognize, or be able to ascertain using no more than routine experimentation, many equivalents to the specific aspects of the disclosure described herein. Such equivalents are intended to be encompassed by the following claims.

Various publications are cited herein, the disclosures of which are incorporated by reference in their entireties.

Although the foregoing invention has been described in some detail by way of illustration and example for purposes of clarity of understanding, it will be obvious that certain changes and modifications can be practiced within the scope of the appended claims.

| SEQUENCE LISTING |
|---|

SEQ ID NO: 1
<US20100291073_1 Sequence 1 from Patent US 20100291073 Organism: *Homo sapiens*
DIQMTQSPSSLSASVGDRVTITCGTSEDIINYLNWYQQKPGKAPKLLIYHTSRLQSGVPSR
FSGSGSGTDFTLTISSLQP
EDFATYYCQQGYTLPYTFGQGTKVEIK SEQ ID NO: 2
<US20100291073_2 Sequence 2 from Patent US 20100291073 Organism: *Homo sapiens*
DIQMTQSPSSLSASVGDRVTITCGTSEDIINYLNWYQQKPGKAPKLLIYHTSRLQSGVPSR
FSGSGSGTDFTLTISSLQP
EDFATYYCQQGYTLPYTFGQGTKVEIKRTVAAPSVFIFPPSDEQLKSGTASVVCLLNNEY
PREAKVQWKVDNALQSGNSQ
ESVTEQDSKDSTYSLSSTLTLSKADYEKHKVYACEVTHQGLSSPVTKSFNRGEC SEQ ID NO: 3
<US20100291073_3 Sequence 3 from Patent US 20100291073 Organism: *Homo sapiens*
EVQLVQSGAEVKKPGASVKVSCKASGYTFTSYVIHWVRQRPGQGLAWMGYINPYNDG
TKYNERFKGKVTITSDRSTSTVY
MELSSLRSEDTAVYLCGREGIRYYGLLGDYWGQGTLVTVSS SEQ ID NO: 4
<US20100291073_4 Sequence 4 from Patent US 20100291073 Organism: *Homo sapiens*
EVQLVQSGAEVKKPGASVKVSCKASGYTFTSYVIHWVRQRPGQGLAWMGYINPYNDG
TKYNERFKGKVTITSDRSTSTVY
MELSSLRSEDTAVYLCGREGIRYYGLLGDYWGQGTLVTVSSASTKGPSVFPLAPSSKSTS
GGTAALGCLVKDYFPEPVTV
SWNSGALTSGVHTFPAVLQSSGLYSLSSVVTVPSSSLGTQTYICNVNHKPSNTKVDKKVE
PKSCDKTHTCPPCPAPELLG
GPSVFLFPPKPKDTLMISRTPEVTCVVVDVSHEDPEVKFNWYVDGVEVHNAKTKPREEQ
YNSTYRVVSVLTVLHQDWLNG
KEYKCKVSNKALPAPIEKTISKAKGQPREPQVYTLPPSRDELTKNQVSLTCLVKGFYPSDI
AVEWESNGQPENNYKTTPP
VLDSDGSFFLYSKLTVDKSRWQQGNVFSCSVMHEALHNHYTQKSLSLSPGK SEQ ID NO: 5
<US20100291073_5 Sequence 5 from Patent US 20100291073 Organism: *Homo sapiens*
DLLPDEKISLLPPVNFTIKVTGLAQVLLQWKPNPDQEQRNVNLEYQVKINAPKEDDYET
RITESKCVTILHKGFSASVRT
ILQNDHSLLASSWASAELHAPPGSPGTSIVNLTCTTNTTEDNYSRLRSYQVSLHCTWLVG
TDAPEDTQYFLYYRYGSWTE
ECQEYSKDTLGRNIACWFPRTFILSKGRDWLAVLVNGSSKHSAIRPFDQLFALHAIDQINP
PLNVTAEIEGTRLSIQWEK
PVSAFPIHCFDYEVKIHNTRNGYLQIEKLMTNAFISIIDDLSKYDVQVRAAVSSMCREAGL
WSEWSQPIYVGNDEHKPLR
EWFVIVIMATICFILLILSLICKICHLWIKLFPPIPAPKSNIKDLFVTTNYEKAGSSETEIEVIC
YIEKPGVETLEDSVF SEQ ID NO: 6
<US20100291073_6 Sequence 6 from Patent US 20100291073 Organism: *Mus musculus*
DLLNHKKFLLLPPVNFTIKATGLAQVLLHWDPNPDQEQRHVDLEYHVKINAPQEDEYDT
RKTESKCVTPLHEGFAASVRT
ILKSSHTTLASSWVSAELKAPPGSPGTSVTNLTCTTHTVVSSHTHLRPYQVSLRCTWLVG
KDAPEDTQYFLYYRFGVLTE
KCQEYSRDALNRNTACWFPRTFINSKGFEQLAVHINGSSKRAAIKPFDQLFSPLAIDQVN
PPRNVTVEIESNSLYIQWEK
PLSAFPPDHCFNYELKIYNTKNGHIQKEKLIANKFISKIDDYSTYSIQVRAAVSSPCRMPGR
WGEWSQPIYVGKERKSLVE
WHLIVLPTAACFVLLIFSLICRVCHLWTRLFPPVPAPKSNIKDLPVVTEYEKPSNETKIEVV
HCVEEVGFEVMGNSTF

SEQ ID NO: 7 - VH CDR1
SYVIH

SEQ ID NO: 8 - VH CDR2
YINPYNDGTKYNERFKG

SEQ ID NO: 9 - VH CDR3
EGIRYYGLLGDY

SEQUENCE LISTING

SEQ ID NO: 10 - VL CDR1
GTSEDIINYLN

SEQ ID NO: 11 - VL CDR2
HTSRLQS

SEQ ID NO: 12 - VL CDR3
QQGYTLPYT

---

What is claimed is:

1. A method of treating asthma by reducing the annual exacerbation rate of asthma, comprising administering subcutaneously to an adult asthma patient a dose of 30 mg once every four weeks for twelve weeks and then once every eight weeks benralizumab or an antigen-binding fragment thereof, wherein the administration reduces the patient's exacerbation rate.

2. The method of claim 1, wherein the asthma is eosinophilic asthma.

3. The method of claim 1, wherein the patient has a blood eosinophil count of at least 300 cells/μl.

4. The method of claim 1, wherein, the patient has a forced expiratory volume ($FEV_1$) of at least 75% predicted value prior to the administration.

5. The method of claim 1, wherein the annual exacerbation rate is reduced by at least 35%.

6. The method of claim 1, wherein the patient uses high-dose inhaled corticosteroids (ICS).

7. The method of claim 1, wherein the patient uses long-acting β2 agonists (LABA).

8. The method of claim 1, wherein the patient has a history of exacerbations.

9. The method of claim 1, wherein the benralizumab or antigen-binding fragment thereof is administered in addition to corticosteroid therapy.

* * * * *